(12) United States Patent
Kuczynski et al.

(10) Patent No.: US 10,955,370 B2
(45) Date of Patent: Mar. 23, 2021

(54) CONTAINER CAP TO TEST VOLATILE ORGANIC COMPOUNDS

(71) Applicant: International Business Machines Corporation, Armonk, NY (US)

(72) Inventors: Joseph Kuczynski, North Port, FL (US); Marvin M. Misgen, Rochester, MN (US); Joseph F. Prisco, Rochester, MN (US); Debra A. Neuman-Horn, Rochester, MN (US); Kevin J. Przybylski, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 232 days.

(21) Appl. No.: 15/878,558

(22) Filed: Jan. 24, 2018

(65) Prior Publication Data
US 2019/0227015 A1    Jul. 25, 2019

(51) Int. Cl.
*G01N 27/02* (2006.01)
*G01N 33/00* (2006.01)
*B01L 3/00* (2006.01)

(52) U.S. Cl.
CPC ............ *G01N 27/028* (2013.01); *B01L 3/502* (2013.01); *B01L 3/50825* (2013.01); *G01N 33/0047* (2013.01); *B01L 2200/0689* (2013.01); *B01L 2200/12* (2013.01); *B01L 2300/023* (2013.01); *B01L 2300/042* (2013.01); *B01L 2300/048* (2013.01); *B01L 2300/0627* (2013.01); *B01L 2300/0645* (2013.01); *B01L 2300/0672* (2013.01)

(58) Field of Classification Search
CPC .................................................. G01N 33/0047
See application file for complete search history.

(56) References Cited

U.S. PATENT DOCUMENTS

| 4,713,164 A | * | 12/1987 | Krietemeier | ......... | G01N 33/497 204/400 |
| 5,770,153 A | * | 6/1998 | Wagner | .................... | G01N 7/00 422/79 |
| 6,903,823 B1 | * | 6/2005 | Muller | .................. | G01N 33/497 356/437 |

(Continued)

FOREIGN PATENT DOCUMENTS

| WO | 2009091402 A1 | 7/2009 |
| WO | 2013158988 A1 | 10/2013 |
| WO | 2014159120 A1 | 10/2014 |

OTHER PUBLICATIONS

Ding et al., "Distributed Sensing for Quality and Productivity Improvements," IEEE Transactions on Automation Science and Engineering, vol. 3, No. 4, Oct. 2006, 16 pages.

(Continued)

*Primary Examiner* — Matthew D Krcha
(74) *Attorney, Agent, or Firm* — Patterson + Sheridan, LLP (57) ABSTRACT

Method and apparatus to test for volatile organic compounds (VOCs), including a cap configured to at least partially seal a container, and a plunger mechanism configured to form a passageway for air to flow from the container into a detection area. A sensor may be attached to the cap and positioned proximate the detection area. The sensor may be configured to detect data relating to a VOC and to generate a signal. A processor may be configured to receive the signal and to determine a result relating to the VOC.

16 Claims, 5 Drawing Sheets

(56) References Cited

U.S. PATENT DOCUMENTS

| | | | |
|---|---|---|---|
| 2006/0078961 A1* | 4/2006 | Chiu | B01L 3/0293 |
| | | | 435/29 |
| 2008/0149584 A1 | 6/2008 | Martinelli | |
| 2009/0301234 A1* | 12/2009 | Risk | G01N 1/2294 |
| | | | 73/864.83 |
| 2011/0119090 A1 | 5/2011 | Lazar | |
| 2014/0120606 A1 | 5/2014 | Wolters et al. | |
| 2015/0087015 A1* | 3/2015 | Bos | B01L 3/50825 |
| | | | 435/34 |
| 2016/0122698 A1 | 5/2016 | Suslick et al. | |

OTHER PUBLICATIONS

Wu, "3D-printed microelectronics for integrated circuitry and passive wireless sensors," Microsystems & Nanoengineering (2015), 1, 15013; doi:10.1038/microanao_2015.13, 9 pages.

Mignani, A. G., et al., "Non-Destructive Testing of Olive Oil Off-Flavors by Means of a Micro-Optic Smart Cap", IEEE Sensors 2008 Conference, 2008.

* cited by examiner

CONTAINER CAP TO TEST VOLATILE ORGANIC COMPOUNDS

BACKGROUND

The present invention relates gaseous emissions detection, and more particularly, to devices to detect volatile organic compounds (VOCs).

VOCs are organic chemicals that have a high vapor pressure at ordinary room temperature. VOCs are present in containers housing certain consumable products, such as olive oil. Some VOCs can have compounding long-term health effects and cause harm to the environment. Detection can require the containers to be opened, and the products to be physically contacted. This practice is time consuming and can lead to unintentional spillage, spoilage, compromised freshness, and contamination.

SUMMARY

According to one embodiment of the present invention, an apparatus to test for VOCs includes a cap configured to at least partially seal a container, and a plunger mechanism configured to form a passageway for air to flow from the container into a detection area. A sensor may be attached to the cap and positioned proximate the detection area. The sensor may be configured to detect specific VOCs and to generate a signal. A processor may be configured to receive the signal and to determine a result relating to the VOC.

According to another particular embodiment, a method of manufacturing a volatile organic compound VOC testing system includes attaching a VOC sensor to a cap configured to at least partially seal a container and forming with a plunger mechanism a passageway for air to flow from the container into a detection area. The method may further sense VOC data in the detection area and display the information relating to the VOC data.

According to another embodiment, a computer program product includes a computer-readable storage medium having computer-readable program code embodied therewith, the computer-readable program code executable by one or more computer processors to receive VOC data sensed by a sensor embedded within a cap positioned above a sealed container, determine a result relating to the VOC data, and to initiate an output of the result to a user.

DETAILED DESCRIPTION

An embodiment includes a novel cap design to detect VOCs from a consumable product whose quality, provenance, or age needs to be verified. The VOCs may be determined without directly contacting the liquid. In one example, a container cap VOC detection system includes an array of head space sensors into a cap of a consumable product bottle. Head space may refer to an unfilled space left above the contents in the product bottle or other sealed container. Direct contact with the product may be avoided while detecting the VOCs.

According to a particular implementation, an embodiment of the system may include a polymer sensor circuit embedded within a cap used to seal a consumer product. An analytic circuit may be used to process signals derived from the polymeric sensor circuits. Additionally, a power circuit (e.g., a remote power source or onboard battery) may be used to power the polymer sensor circuit and analytic circuit. A mechanical chamber may be used to expose the polymer sensor circuit to the head space of the cap to active components in the product.

A sample time may be empirically determined. For instance, the sample time may be based on what is being sampled and the response time of the sensor array. The head space may be purged, or vented, to ambient air when desired. Such a purge may be beneficial, for instance, between sampling the product VOCs.

VOCs have a high vapor pressure at room temperature. The resultant volatility causes molecules to evaporate from liquids and enter the surrounding air at a predictable and calculated rate under defined conditions. For example, the vapor pressure of olive oil can be predicted at room temperature using the Clausius-Clapeyron relation.

The container cap VOC detection system may make use of this principle to sample, detect, and analyze VOCs in a product container multiple times before consumer use to understand product quality and freshness.

Figure 1:
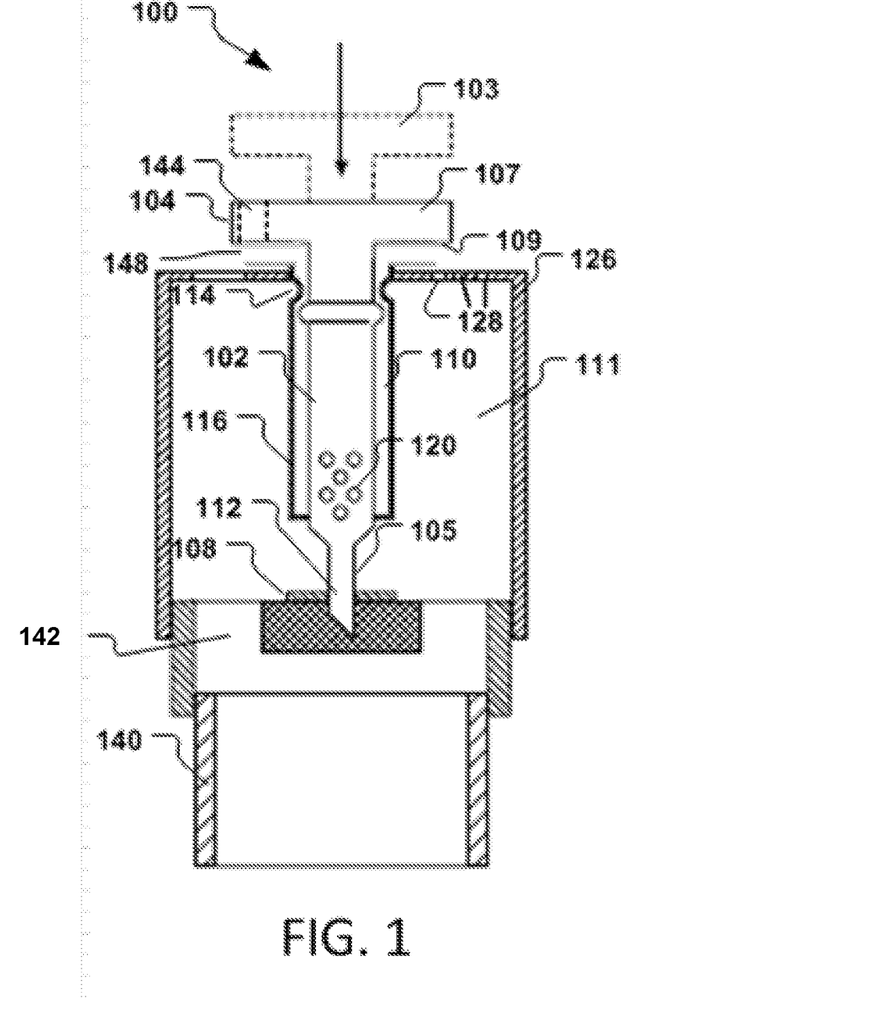
FIG. 1 is a perspective view of a container cap VOC detection system consistent with an embodiment.

FIG. 1 is an embodiment of a container cap VOC detection system 100 that includes a sample plunger 102. The sample plunger 102 may include a selector 104, in addition to the sample plunger 102. The sample plunger 102 may be initially in an up position 103 (denoted by dashed lines) above a puncture seal 108. The puncture seal 108 may be pliable and self-sealing around a contacting part of an outside surface 105 of the sample plunger 102. The puncture seal 108 may permit migration of VOCs from an interior space 142 of the container 140 only through the inside of the sample plunger 102 and not around the outside of the puncture seal 108 as physically contacted by the puncture seal 108.

During a first sample use, the sample plunger 102 may be depressed to a down position 107. The downward movement of the sample plunger 102 may cause it to rupture the puncture seal 108. The sample plunger 102 may be hollow, like a syringe. The action may allow VOCs to enter a sample head space 110 through an interior portion 112 and via apertures 120 of the sample plunger 102. The head space 110 may be at least partially defined by a sleeve 116.

As shown in FIG. 1, a sleeve retainer detent 114 may retain sample plunger 102 in a fixed position within the sleeve 116 when the sample plunger 102 is depressed for the first time. The sleeve retainer detent 114 may further prevent the sample plunger 102 from backing out of the depressed position.

The puncture seal 108 may be constructed from a flexible, self-healing silicone or other material suited for maintaining long term product freshness. Once the puncture seal 108 is penetrated, the sleeve 116 and plunger sealing may be adequate for longer term product freshness, such as when the product is in a warehouse or on a store shelf for longer periods of time.

Figure 2:
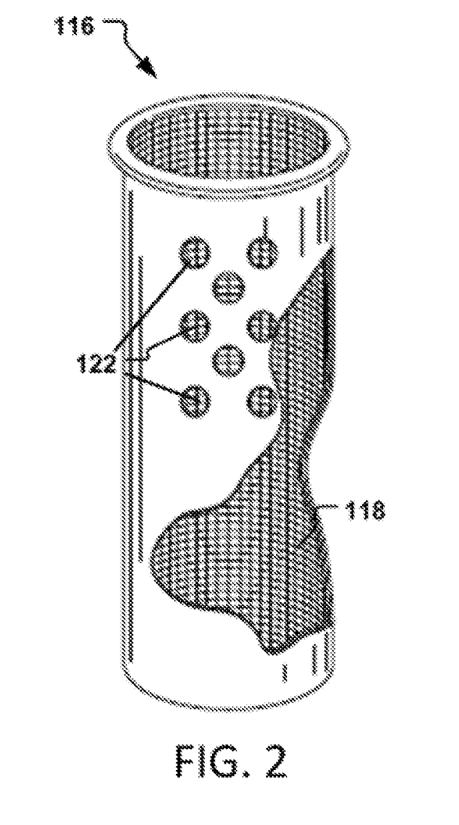
FIG. 2 is a perspective view of a sleeve mechanism of FIG. 1.

The sleeve 116, as also shown FIG. 2, may be manufactured from a homogeneous material or may be supplied with a coating 118. An illustrative coating may include a thin silicone rubber on an inner wall surface that is pliable with friction against the sample plunger 102. The friction may allow slight resistance to a rotation of the sample plunger 102 and may seal plunger vent holes 120 when not aligned with sleeve vent holes 122.

Figure 3:
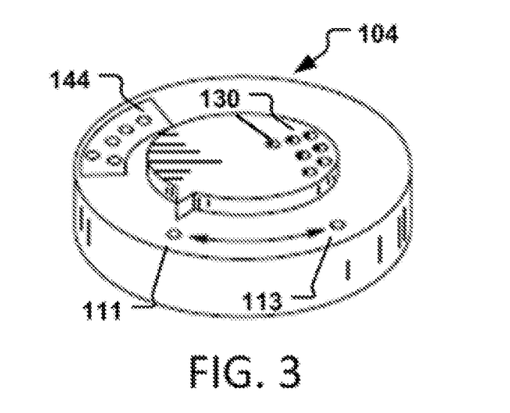
FIG. 3 is a perspective view of a selector mechanism of FIG. 1.

The selector 104, as also shown in FIG. 3, may comprise an actuating indicator forming a top of the sample plunger 102. A bottom of the actuator surface may ride on a top surface of a cap 126 when the selector 104 is rotated. Gasket or coating materials (not shown) on a bottom surface 109 of the selector 104 may allow the selector 104 to function as a seal for purge vents 128. The selector 104 may be rotated to one of two positions: a purging position 111 and a sampling position 113.

The purging position 111 may align purge vents 130 located in the top of the selector 104 with the vent holes 128 in the top of the cap 126. This selected arrangement may allow evacuation/purging of VOCs from the head space 110 resulting from the high vapor pressure. While in purging position 111, the sleeve vents 122 may be unaligned with the sample plunger vents 120. As such, the seal coating 118 may prevent VOCs from entering the sampling head space 110.

The sampling position 113 may close off the purge vents 128 in the cap 126 and align the sleeve vents 122 with the sample plunger vents 120. This alignment may allow VOCs from the product container 140 and plunger 102 to enter the sampling head space 110 through the aligned vent holes 120, 122. In the sampling position, time may be allowed to saturate the sampling head space 110 with VOCs. The time may be adequate allowing a sense circuit 144 to detect the VOCs escaping at 148 from the sleeve 116.

The detection may be initiated once an electrical and data connection is made to an off-board computer (not shown). To this end, the sense circuit 144 may include VOC detectors positioned near or on the bottom surface 109 of the selector 104. The computer may then interface with power and data connections 146 of the sense circuit 144. The sense circuit 144 may electronically interrogate the VOC sample and determine product quality. Another embodiment may include a processor having some or all of the functionality of the computer embedded inside of the cap.

Figure 4:
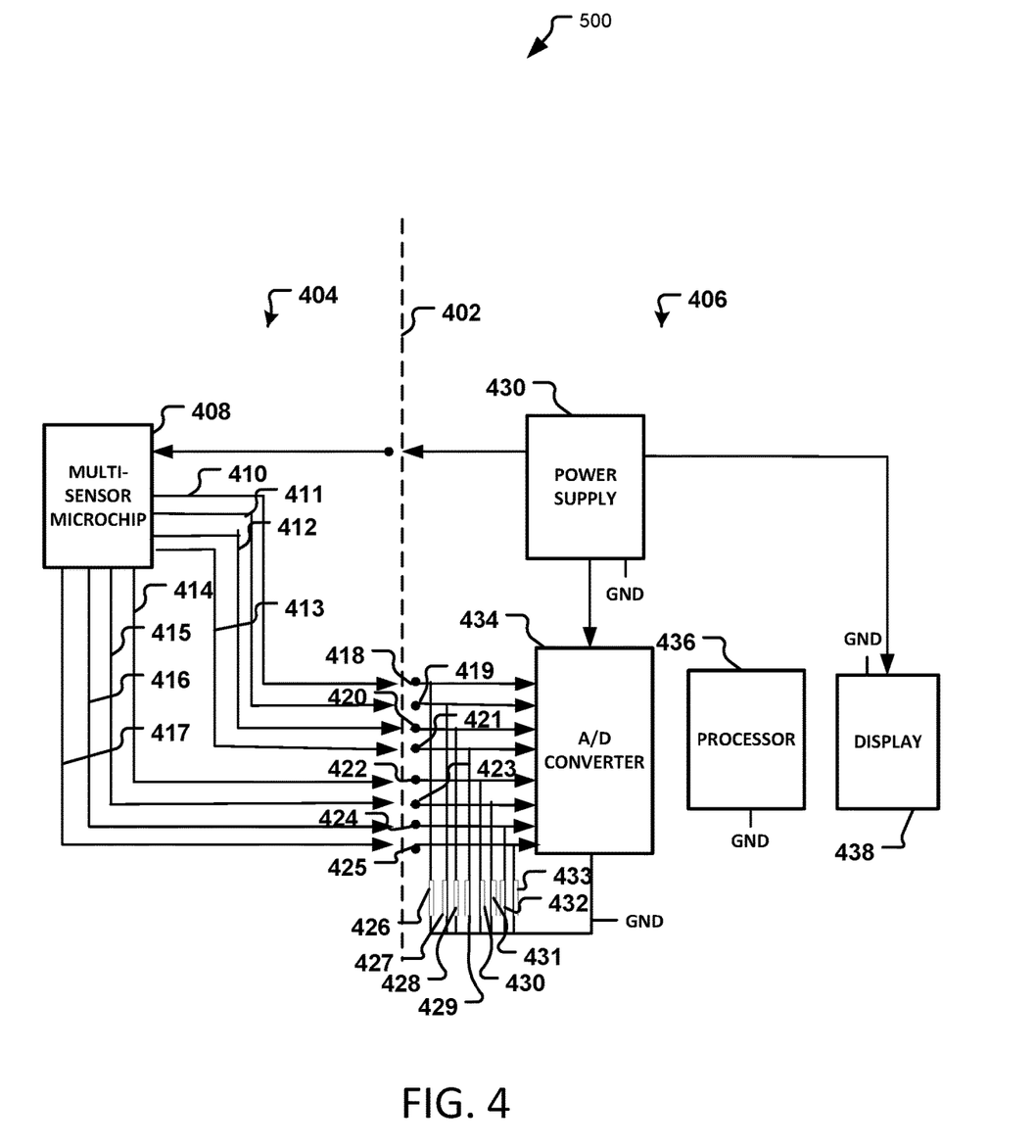
FIG. 4 is a functional diagram of an embodiment of an apparatus comprising a system and associated circuitry that senses VOCs using a cap.

FIG. 4 is a functional diagram of an embodiment of an apparatus 400 comprising a system and associated circuitry that senses VOCs using a cap that seals extra virgin olive oil. The diagram includes a line 402 demarcating functions performed at the cap side 404 and those performed at computing device side 406. However, other embodiments may position modules differently. For instance, resisters 426-433 could be on the cap side 404, rather than as shown on the computing device side 406. In another embodiment, all of the modules of FIG. 4 may be included on the cap side 404.

Turning more particularly to the drawing, a multi-sensor microchip 408 may be positioned to sense VOCs from a product container. Sensor outputs 410-417 may be provided to interface contacts 418-425. The contacts 418-425 may be respectively wired to reference resisters 426-433, as well as to an analog-to-digital (A/D) converter 434. Output from the A/D converter 434 may be provided to a processor 436 for analysis. The microchip may receive power when connected to a supply 440.

In one particular example, the microchip 408 may include an array of sensors comprising traces of materials that are exposed to air from the head space, and that react to VOCs. The reaction may cause a change in chemical composition that changes the impedance of the circuit. The processor 436 of an embodiment may identify VOC parameters based on the impedance values. A display 438 may receive data from the processor 436 and communicate results to a user.

Figure 5:
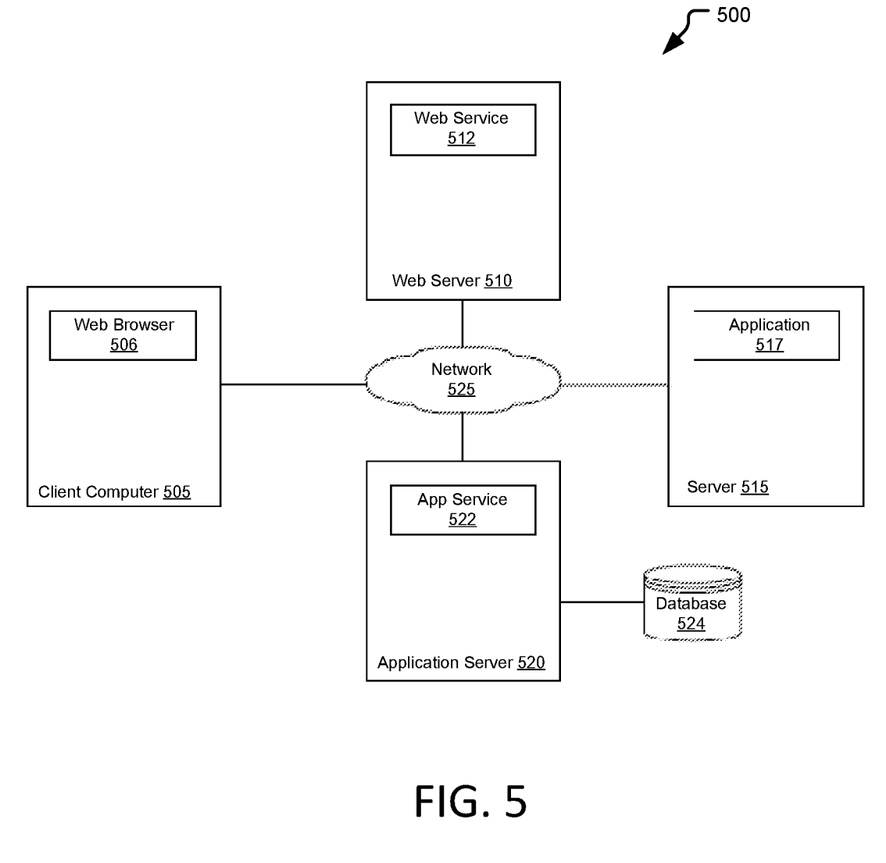
FIG. 5 illustrates an example computing environment according to one embodiment.

FIG. 5 illustrates an example computing environment 500 according to one embodiment. As shown, the computing environment 500 includes a client computer 505, a web server 510, a server 515, and an application server 520. The client computer 505 may be a physical system (e.g., a desktop, laptop computer, mobile device, etc.) or a virtual computing instance executing in the cloud. The client computer 505 includes a web browser 506. A user may access data services through the web browser 506 over a network 525 (e.g., the Internet).

For instance, a user may access a web service 512 executing on a web server 510. In one embodiment, the web service 512 provides a web interface for an application server 520 (e.g., executing an application service 522). More specifically, the application service 522 provides a database 524.

Figure 6:
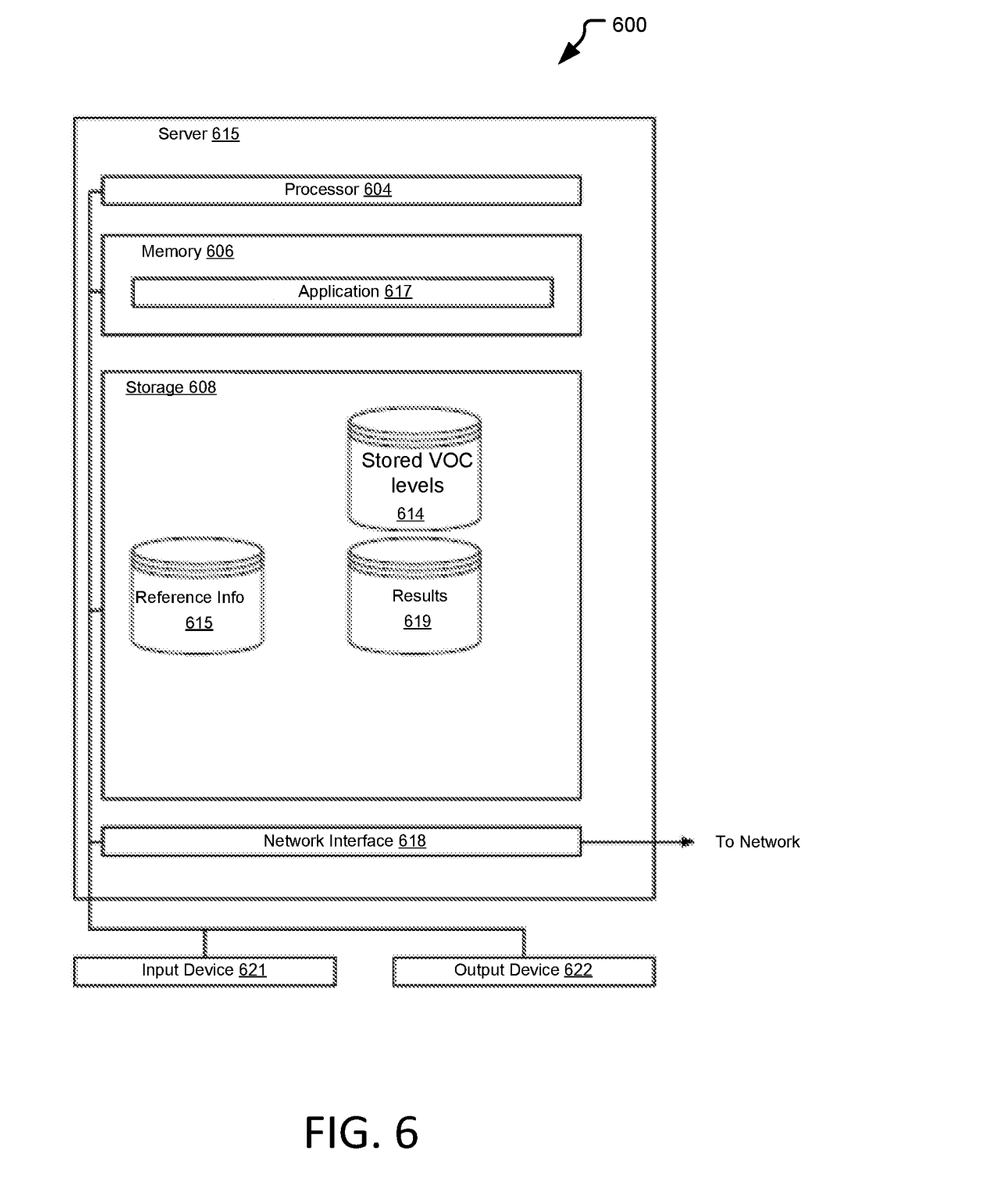
FIG. 6 further illustrates a server of FIG. 5, according to one embodiment.

FIG. 6 further illustrates the server 615, according to one embodiment. The server 615 generally includes a processor 604 connected via a bus to a memory 606, a network interface device 618, a storage 608, an input device 621, and an output device 622. The server 615 is generally under the control of an operating system. Examples of operating systems include the UNIX operating system, versions of the Microsoft Windows operating system, and distributions of the Linux operating system. (UNIX is a registered trademark of The Open Group in the United States and other countries. Microsoft and Windows are trademarks of Microsoft Corporation in the United States, other countries, or both. Linux is a registered trademark of Linus Torvalds in the United States, other countries, or both.) More generally, any operating system supporting the functions disclosed herein may be used. The processor 604 is included to be representative of a single CPU, multiple CPUs, a single CPU having multiple processing cores, and the like. Similarly, the memory 606 may be a random access memory. While the memory 606 is shown as a single identity, it should be understood that the memory 606 may comprise a plurality of modules, and that the memory 606 may exist at multiple levels, from high speed registers and caches to lower speed but larger DRAM chips. The network interface device 618 may be any type of network communications device allowing the navigation server 510 to communicate with other computers via the network 525.

The storage 608 may be a persistent storage device. Although the storage 608 is shown as a single unit, the storage 608 may be a combination of fixed and/or removable storage devices, such as fixed disc drives, solid state drives, removable memory cards, optical storage and network storage systems.

As shown, the memory 606 contains the application 617, which is an application generally executed to take actions described herein. Storage 608 contains stored VOC levels 614, VOC reference information 615, and results 619.

The input device 622 may provide a keyboard and/or a mouse, etc. The output device 622 may be any conventional display screen. Although shown separately from the input device 621, the output device 622 and input device 621 may be combined. For example, a display screen with an integrated touch-screen may be used.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the following, reference is made to embodiments presented in this disclosure. However, the scope of the present disclosure is not limited to specific described embodiments. Instead, any combination of the following features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the following aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Aspects of the present invention may take the form of an entirely hardware embodiment, an entirely software embodiment (including firmware, resident software, microcode, etc.) or an embodiment combining software and hardware aspects that may all generally be referred to herein as a "circuit," "module" or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the foregoing is directed to embodiments of the present invention, other and further embodiments of the invention may be devised without departing from the basic scope thereof, and the scope thereof is determined by the claims that follow.

What is claimed is:

1. An apparatus comprising:
    a cap configured to at least partially seal a container, the cap comprising a venting aperture;
    a plunger mechanism configured to form a passageway for air to flow from the container into a detection area, wherein the plunger mechanism includes a first aperture, a purging aperture, and a selector;
    a sleeve positioned circumferentially around the plunger mechanism, wherein the sleeve includes a second aperture that aligns with the first aperture to form the passageway when the selector is in a first position, wherein the purging aperture is unaligned with the venting aperture when the selector is in the first position, and wherein, when the selector is in the second position, the second aperture is unaligned with the first aperture and the purging aperture is aligned with the venting aperture;
    a sensor attached to the cap and positioned proximate the detection area, the sensor configured to detect data relating to a volatile organic compound (VOC) and to generate a signal; and
    a processor configured to receive the signal and to determine a result relating to the VOC.

2. The apparatus of claim 1, wherein the sensor is a polymer sensor circuit embedded within the cap.

3. The apparatus of claim 1, wherein the sensor is one of an array of sensors configured to sample air from a head space.

4. The apparatus of claim 1, wherein the VOC data is sensed while avoiding direct contact with a fluid producing the VOC.

5. The apparatus of claim 1, further comprising a power circuit configured to provide power to the processor and sensor.

6. The apparatus of claim 1, wherein the sensor is exposed to the VOC for a time period determined according to a material being sampled.

7. The apparatus of claim 1, wherein the sensor is exposed to a response time of the sensor.

8. The apparatus of claim 1, further comprising a display configured to display the result.

9. The apparatus of claim 1, wherein the cap is further configured to vent a head space.

10. The apparatus of claim 1, further comprising a puncture seal positioned between the plunger and the container.

11. The apparatus of claim 1, wherein the selector is configured to rotate to transition from the first position to the second position.

12. The apparatus of claim 1, wherein the container remains sealed after the plunger mechanism is depressed.

13. An apparatus comprising:
    a cap configured to at least partially seal a container, the cap comprising a venting aperture;
    a plunger mechanism configured to form a passageway for air to flow from the container into a detection area, wherein the plunger mechanism includes a first aperture, a purging aperture, and a selector;
    a sleeve positioned circumferentially around the plunger mechanism, wherein the sleeve includes a second aperture that aligns with the first aperture to form the passageway when the selector is in a first position, wherein the purging aperture is unaligned with the venting aperture when the selector is in the first position, and wherein, when the selector is in a second position, the second aperture is unaligned with the first aperture and the purging aperture is aligned with the venting aperture;
    a sensor positioned proximate the detection area, the sensor configured to detect data relating to a volatile organic compound (VOC).

14. The apparatus of claim 13, wherein the sensor is a polymer sensor circuit embedded within the cap.

15. The apparatus of claim 13, wherein the VOC data is sensed while avoiding direct contact with a fluid producing the VOC.

16. The apparatus of claim 13, further comprising a power circuit configured to provide power to the sensor.

* * * * *